(12) United States Patent
Streeter et al.

(10) Patent No.: US 10,485,976 B2
(45) Date of Patent: Nov. 26, 2019

(54) INTRACARDIOVASCULAR ACCESS (ICVA™) SYSTEM

(75) Inventors: Richard B. Streeter, Winchester, MA (US); John R. Liddicoat, Sewickley, PA (US); Todd F. Davenport, Andover, MA (US)

(73) Assignee: Medtronic, Inc., Minneapolis, MA (US)

( * ) Notice: Subject to any disclaimer, the term of this patent is extended or adjusted under 35 U.S.C. 154(b) by 3397 days.

(21) Appl. No.: 11/115,087

(22) Filed: Apr. 26, 2005

(65) Prior Publication Data

US 2005/0261669 A1 Nov. 24, 2005

Related U.S. Application Data

(63) Continuation of application No. 10/014,699, filed on Oct. 26, 2001, now Pat. No. 6,890,330.
(Continued)

(51) Int. Cl.
*A61N 1/36* (2006.01)

(52) U.S. Cl.
CPC .................................. *A61N 1/36114* (2013.01)

(58) Field of Classification Search
CPC .......... A61B 2017/00218; A61B 2017/00969; A61B 2017/003; A61B 2017/0237;
(Continued)

(56) References Cited

U.S. PATENT DOCUMENTS 3,334,629 A  8/1967  Cohn
3,409,013 A  11/1968  Berry
(Continued)

FOREIGN PATENT DOCUMENTS

CN  2007-100074433  1/2007
DE        3640745    6/1987
(Continued)

OTHER PUBLICATIONS

Jansen et al, "Less invasive off pump CABG using a suction device for immobilization: the octopus method" Eur J Cardio-thoracic Surg, vol. 12, 1997, pp. 406-412.*
(Continued)

*Primary Examiner* — Carl H Layno
*Assistant Examiner* — Michael J Lau
(74) *Attorney, Agent, or Firm* — Dicke, Billig & Czaja, PLLC

(57) ABSTRACT

Apparatus is disclosed for providing access to a functioning vascular system of a patient, the apparatus comprising: a main body having sidewalls defining an interior region and an exterior region, a bottom end and a top end; a base being formed at the bottom end of the main body, securing means being configured on the base so as to allow attachment and formation of a seal between the base and the functioning vascular system of the patient, and the base being configurable to provide a passageway from the interior region of the main body to the functioning vascular system of the patient; and a cover being formed at the top end of the main body, wherein the cover provides a barrier between the interior region and the exterior region at the top end of the main body.

5 Claims, 16 Drawing Sheets

Related U.S. Application Data

(60) Provisional application No. 60/243,869, filed on Oct. 27, 2000.

(58) Field of Classification Search
CPC ...... A61B 2017/0243; A61B 2017/081; A61B 2017/3425–3429; A61B 2017/3449; A61B 2017/3466; A61B 2017/3488; A61B 17/0218; A61B 17/085; A61B 17/3423; A61B 17/3468; A61M 39/02; A61M 2039/062–0686
USPC .................................. 606/11, 139, 201–246
See application file for complete search history.

(56) References Cited

U.S. PATENT DOCUMENTS

| | | |
|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,082,005 A | 1/1992 | Kaldany |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,316,541 A | 5/1994 | Fischer |
| 5,327,774 A | 7/1994 | Nguyen et al. |
| 5,332,402 A | 7/1994 | Teitelbaum et al. |
| 5,336,171 A | 8/1994 | Sugarbaker |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,865,731 A * | 2/1999 | Lenox ............... A61B 17/0206 600/232 |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |

(56) References Cited

U.S. PATENT DOCUMENTS

| | | | |
|---|---|---|---|
| 5,906,577 A * | 5/1999 | Beane et al. ............... 600/207 |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,922 A | 9/1999 | MacLeod |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,024,736 A | 2/2000 | de la Torre et al. |
| 6,027,525 A | 2/2000 | Suh et al. |
| 6,029,671 A | 2/2000 | Stevens et al. |
| 6,042,539 A * | 3/2000 | Harper et al. ............... 600/201 |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,689 B1 * | 12/2002 | Kaplan et al. ............... 606/139 |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,547,725 B1 * | 4/2003 | Paolitto ............. A61B 17/0206 600/201 |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,837,851 B1 * | 1/2005 | Valentini ............. A61B 17/0206 600/210 |
| 6,840,246 B2 * | 1/2005 | Downing ............... A61F 2/2466 128/898 |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |

(56) References Cited

U.S. PATENT DOCUMENTS

| | | |
|---|---|---|
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,158 B2 * | 2/2008 | Taylor ............ A61B 17/00 128/897 |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,651,499 B2 * | 1/2010 | Eckman ......... A61B 17/320016 606/86 R |
| 7,806,919 B2 | 10/2010 | Bloom et al. |
| 2001/0002445 A1 | 3/2001 | Vesely |
| 2001/0001314 A1 | 5/2001 | Davison et al. |
| 2001/0002429 A1* | 5/2001 | Hu ............ A61B 17/0206 600/210 |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |

(56) References Cited

U.S. PATENT DOCUMENTS

| | | |
|---|---|---|
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |

(56) References Cited

U.S. PATENT DOCUMENTS

| | | |
|---|---|---|
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 46 692 A1 | 6/1997 |
| EP | 1057460 A1 | 6/2000 |
| EP | 1255510 | 11/2002 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 04/019825 | 3/2004 |
| WO | 04/089250 | 10/2004 |
| WO | 05/004753 | 1/2005 |
| WO | 05/046528 | 5/2005 |
| WO | 06/026371 | 3/2006 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal Sep. 22, 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal Sep. 22, 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

(56) References Cited

OTHER PUBLICATIONS

Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, Edwards' United Kingdom action for invalidity, Claim No. Hc 08CO0934 (83 pages).
Expert report of Dr. Nigel Buller, non-confidential annex—infringement, dated Jan. 12, 2009, Edwards' United Kingdom action for invalidity, Claim No. HC 08CO0934 (12 pages).
Expert report of Dr. Rodolfo Quijano, dated Jan. 9, 2009, Edwards' United Kingdom action for invalidity, Claim No. HC 08CO0934 (18 pages).
First Expert report of Prof. David Williams, dated Jan. 12, 2009, Edwards' United Kingdom action for invalidity, Claim No. HC 08CO0934 (41 pages).
First Expert report of Prof. Martin Rothman, dated Jan. 12, 2009, *Edwards Lifesciences and Cook Biotech*, Edwards' United Kingdom action for invalidity, Claim No. HC 08CO0934 (64 pages).
Fourth Expert report of Prof. Martin Rothman, dated Apr. 22, 2009, *Edwards Lifesciences and Cook Biotech*, Edwards' United Kingdom action for invalidity, Claim No. HC 08CO0934 (10 pages).
Second Expert report of Dr. Nigel Buller, dated Feb. 25, 2009, Edwards' United Kingdom action for invalidity, Claim No. HC 08CO0934 (24 pages).
Second Expert report of Dr. Rodolfo Quijano, dated Feb. 26, 2009, Edwards' United Kingdom action for invalidity, Claim No. HC 08CO0934 (6 pages).
Second Expert report of Prof. David Williams, dated Feb. 5, 2009, Edwards' United Kingdom action for invalidity, Claim No. HC 08CO0934 (15 pages).
Second Expert report of Prof. Martin Rothman, dated Feb. 5, 2009, *Edwards Lifesciences and Cook Biotech*, Edwards' United Kingdom action for invalidity, Claim No. HC 08CO0934 (11 pages).
Third Expert report of Dr. Nigel Buller, dated Apr. 21, 2009, Edwards' United Kingdom action for invalidity, Claim No. HC 08CO0934 (6 pages).
Third Expert report of Dr. Rudolfo Quijano, dated Apr. 27, 2009, Edwards' United Kingdom action for invalidity, Claim No. HC 08CO0934 (3 pages).
Third Expert report of Prof. David Williams, dated Apr. 22, 2009, Edwards' United Kingdom action for invalidity, Claim No. HC 08CO0934 (9 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Dr. Anthony C. Lunn (7 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Witness statement of Stanton Rowe (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Witness statement of Stanton Rowe (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
PVT slides naming Alain Cribier, Martin Leon, Stan Rabinovich and Stanton Rowe (16 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Expert Rebuttal Report of Prof. Martin T. Rothman (32 pages) redacted, *Edwards v. CoreValve*, U.S. District Court, District of Delaware, Case No. 08-091, dated Jul. 29, 2009.
Expert Report of Prof. Martin T. Rothman (74 pages) redacted, *Edwards v. CoreValve*, U.S. District Court, District of Delaware, Case No. 08-091, dated Jun. 29, 2009.
First Expert report of Richard A. Hillstead (41 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Reply Expert report of Richard A. Hillstead (9 pages), *Corevalve, Inc. v. Edwards Lifesciences AG and Edwards Lifesciences PVT,*

(56) References Cited

OTHER PUBLICATIONS

*Inc.*, High Court of Justice—Chancery Division Patents Court, United Kingdom, Case No. HC-07-C01243.

\* cited by examiner

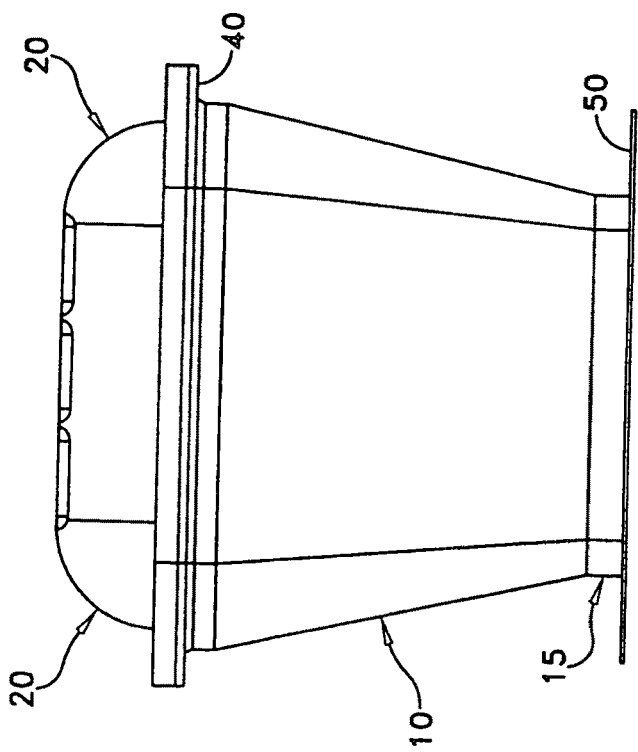
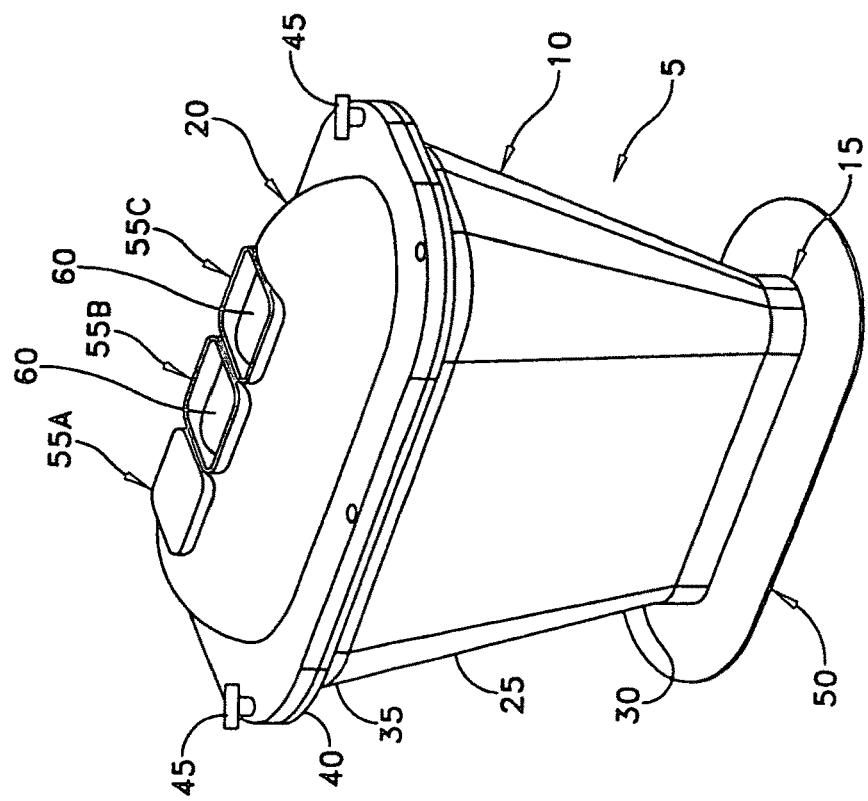

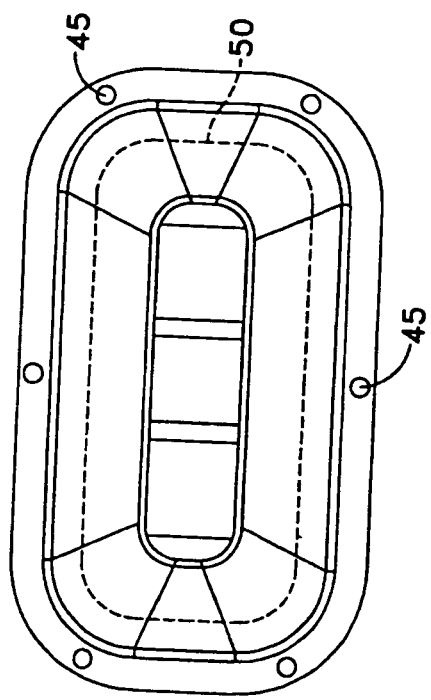
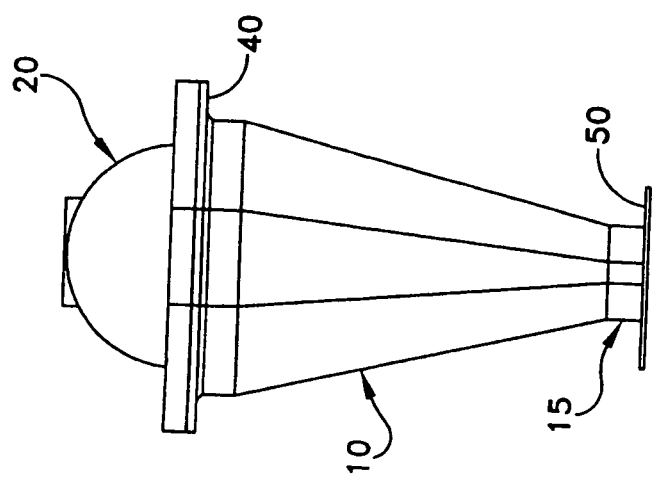
FIG. 4
FIG. 3

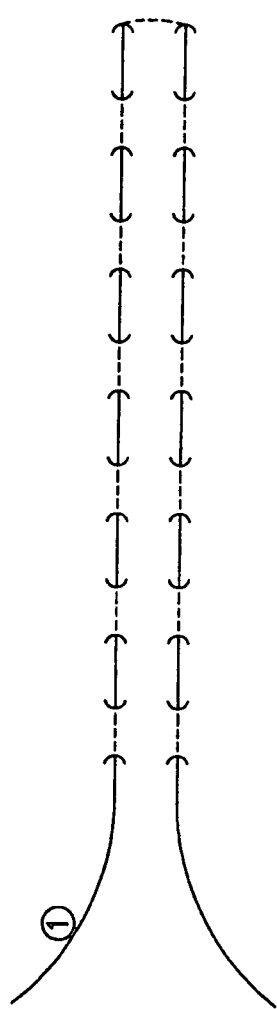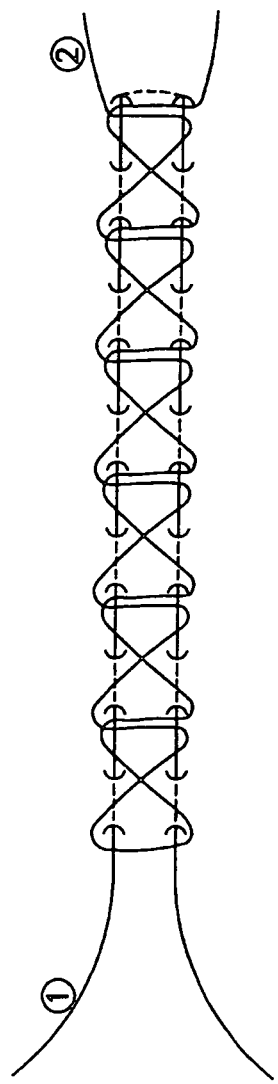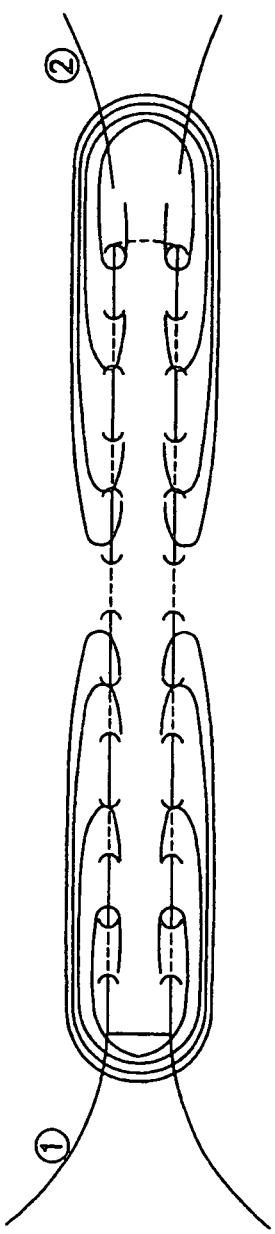

INTRACARDIOVASCULAR ACCESS (ICVA™) SYSTEM

REFERENCE TO PENDING PRIOR APPLICATIONS

This patent application is a continuation of U.S. application Ser. No. 10/014,699, filed on Oct. 26, 2001 by Richard B. Streeter et al. that issued as U.S. Pat. No. 6,890,330 on May 10, 2005, which claims benefit of pending prior U.S. Provisional Patent Application Ser. No. 60/243,869, filed Oct. 27, 2000 by Richard B. Streeter et al. for INTRACARDIOVASCULAR ACCESS (ICVA™) SYSTEM, which disclosures are hereby incorporated herein by reference.

FIELD OF THE INVENTION

This invention relates to medical devices and procedures in general, and more particularly to medical devices and procedures relating to the cardiovascular system.

BACKGROUND OF THE INVENTION

In standard surgical practice, access to cardiac valves and internal cardiac structures is achieved with the use of cardiopulmonary bypass cardiac arrest and incision into the arrested heart or aorta. Using currently available technology, all cardiac valvular operations require such an approach.

It is well-known that cardiopulmonary bypass and cardiac arrest are associated with significant morbidity and mortality. Recognition of the damaging effects of cardiopulmonary bypass has been the impetus for important advances in beating heart coronary artery bypass grafting. To date, however, it is believed that there are no clinically applicable techniques to perform cardiac valve surgery without using a heart-lung machine. Therefore, cardiac valve surgery currently requires a major operation that includes all of the complications attributable to cardiopulmonary bypass.

In prior U.S. Provisional Patent Application Ser. Nos. 60/117,599, filed on 27 Jan. 1999, 60/152,135, filed on 25 Aug. 1999, 60/161,934, filed on 28 Oct. 1999, 60/215,542, filed on 30 Jun. 2000, and 60/230,756, filed on 7 Sep. 2000, and in pending PCT Patent Application No. PCT/US00/02126, filed on 27 Jan. 2000, which patent applications are hereby incorporated herein by reference, there are disclosed various devices and procedures to facilitate cardiac valve surgery on a beating heart. An important part of any such system is a safe technique for establishing direct intracardiovascular access to the heart, cardiac valves, and the so-called great vessels. Such access must allow the safe introduction of instruments into the cardiovascular system, prevent entry of air into the cardiovascular system, and prevent excessive bleeding. In this respect it should be appreciated that it is generally essential to avoid the introduction of air into the vascular system of the patient, since this could result in serious complications, or even death, for the patient. Another important part of the invention is to enable the simplified opening and closure of incisions into the cardiovascular system.

SUMMARY OF THE INVENTION

In accordance with the present invention, there is provided a system which is adapted to facilitate safe intravascular access to any cardiac or vascular structure. The system is attached to the cardiovascular structure, using suture or sutureless fixation. Instruments may then be introduced into the system. The system is then partially or completely filled with saline, carbon dioxide, or other substance so as to provide an air-free environment, while also purging air from the previously inserted devices. The cardiovascular structure is then opened with a scalpel or other cutting instrument which, if desired, may be integral to the system. Valves on the system permit controlled passage of instruments into the cardiovascular system without excessive back bleeding. At the completion of the procedure, the system is removed, in whole or in part, and hemostasis is achieved by a means that may include suturing or stapling. Hemostasis may also occur during, or prior to, removal of the system.

The system is not necessarily a stand alone device. The system's features and function can be incorporated into a surgical instrument, for use in vascular surgical procedures.

The system has a specific advantage over cannullae in that large objects or devices may be passed through the system's large opening and into the patient's vascular system. Typically, cannullae only allow access for relatively long, narrow instruments.

By way of further example but not limitation, other specific "beating-heart" applications of the invention can include:

| Access Site | Structure (s) | Purpose |
| --- | --- | --- |
| Right Atrium | Tricuspid Valve | Repair, Replace |
| | Pulmonary Valve | Repair, Replace |
| Left Ventricle | Chordae Tendenae | Repair |
| | Septum | Repair |
| | Aortic Valve | Repair, Replace |
| | Mitral Valve | Repair, Replace |
| | Implanted Pumps | Repair, Clot Removal |
| | Implanted Pacemaker Leads | Removal, Exchange, Functional Testing |
| Right Ventricle | Tricuspid and Pulmonic Valves | Repair, Replace |
| | Septum | Repair |
| | Implanted Pumps | Repair, Clot Removal |
| | Implanted Pacemaker Leads | Removal, Exchange, Functional Testing |

While the system may be used for a wide range of applications, several specific applications are anticipated.

For example, it is anticipated that the system will be affixed to the left atrium of the heart, and/or to the pulmonary veins, in order to allow direct access to the mitral valve. Instruments can then be introduced through the system to perform mitral valve repair or replacement, with or without the use of cardiopulmonary bypass.

Furthermore, in beating heart aortic valve surgery, the system could be affixed to the aorta or to the left atrium. Instruments and an aortic prosthesis could then be introduced to the vascular system of the patient through the system.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 1 is a perspective view of a system formed in accordance with the present invention;

FIG. 2 is a front view of the system shown in FIG. 1;

FIG. 3 is a side view of the system shown in FIG. 1;

FIG. 4 is a bottom view of the system shown in FIG. 1;

FIGS. 5A-5C illustrate the formation and closure of a pair of pursestring stitches which may be used in conjunction with the present invention;

DETAILED DESCRIPTION OF THE PREFERRED EMBODIMENTS

Figure 6:
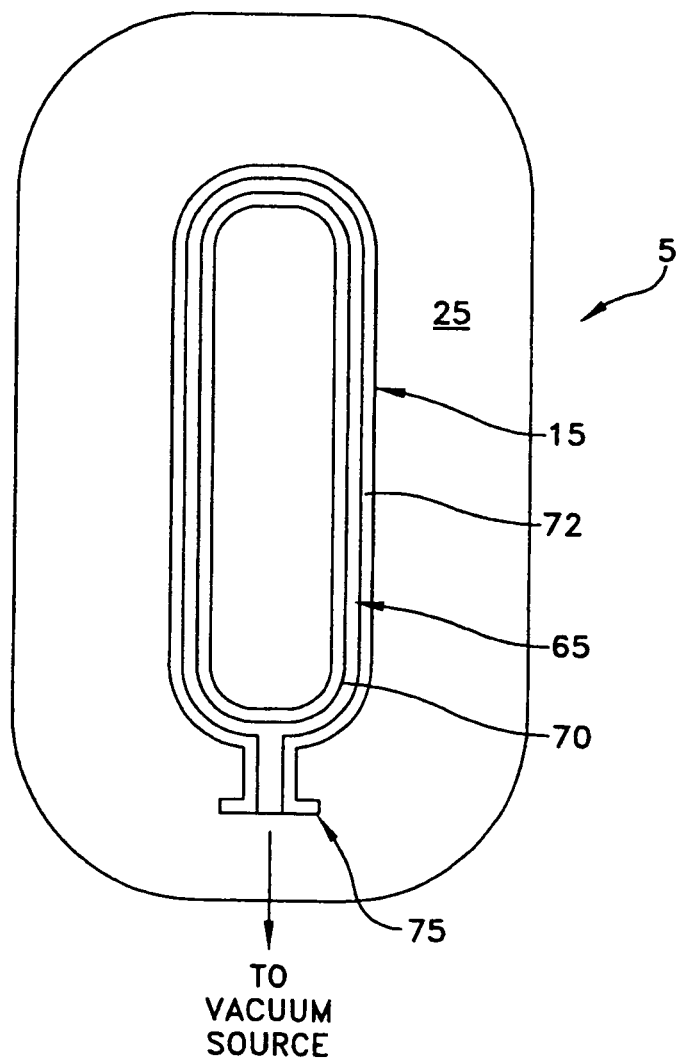
FIG. 6 is a bottom view of an alternative form of the invention.

Looking now at FIGS. 1-4, there is shown a new system 5 which may be used to gain safe and easy air free access to the functioning (or operating) vascular system of a patient. System 5 generally comprises a main body 10, a base 15 and a cover 20.

Main body 10 is a hollow structure and comprises a tapered wall 25 having a bottom end 30 and a top end 35. Tapered wall 25 is preferably formed out of a flexible, clear plastic material, e.g., urethane. The bottom end 30 of tapered wall 25 is connected to base 15 as shown, e.g., by being formed integral with base 15. The top end 35 of tapered wall 25 includes a mount 40 whereby cover 20 may be removably mounted to main body 10, e.g., with thumb screws 45. Mount 40 is preferably formed out a substantially rigid, clear plastic material, e.g., polycarbonate.

Base 15 is a hollow structure which preferably includes a stitching cuff 50 extending around the perimeter of base 15. Stitching cuff 50 permits the system 5 to be secured to a cardiovascular structure, e.g., to the wall of the left atrium of the heart. Base 15 is preferably formed out of a flexible, clear plastic material, e.g., urethane. Stitching cuff 50 is preferably formed out of a clinically acceptable fabric, e.g., Dacron.

Cover 20 is preferably adapted to be removably attached to mount 40 of main body 10. Cover 20 preferably includes several (e.g., three) ports 55 for gaining access to the interior of the system. One of these ports, e.g., port 55A, may comprise the base for a Luer lock fitting or, if desired, may comprise the entire Luer lock fitting. Others of the ports, e.g., ports 55B and 55C, may comprise passageways for instruments. Preferably such instrument ports (e.g., ports 55B and 55C) include penetrable seals 60 of the sort well known in the art for minimizing the flow of fluid through the instrument ports, both when instruments are being passed through the instrument ports and when instruments are not being passed through the instrument ports. Cover 20 is preferably formed out of a substantially rigid, clear plastic material, e.g., polycarbonate.

System 5 may be used to gain safe and easy access to the cardiovascular system of a patient.

By way of example but not limitation, system 5 may be used to gain safe and easy access to the left atrium of a beating heart, whereby to perform a mitral valve replacement or repair while the heart is beating.

In such a procedure, the surgeon first chooses an access site on the surface of the heart, adjacent to the patient's left atrium.

Next, a special running stitch may be pre-placed at the access site. This running stitch is preferably a modified pursestring stitch formed out of two separate pursestring stitches, as shown in FIGS. 5A and 5B which, when subsequently pulled tight, will gather together tissue, as shown in FIG. 5C. The running stitch is placed about the perimeter of the site where the incision will be made, such that, at the conclusion of the procedure, the free ends of the pursestring stitches may be pulled, whereby to close the incision, as will hereinafter be discussed in further detail.

Then the prosthesis (i.e., the artificial valve) is placed in the interior of the system's main body 10, and cover 20 is secured to the top of main body 10 (e.g., with thumb screws 45).

At this point, system 5 is secured to the wall of the heart so that the system's base 15 encircles the running stitch at the incision site. System 5 may be secured to the wall of the left atrium by suturing its stitching cuff 50 to the wall of the beating heart so as to form a substantially fluidtight seal, or a more complex stapling device may be used to secure system 5 to the wall of the left atrium.

Next, carbon dioxide may be introduced into blood lock 5 to displace air from the system. Then a saline source (not shown) is connected to the Luer connector of the system, and the lock is filled with saline.

At this point the system is gently shaken, while attached to the wall of the heart, so as to free up any gas bubbles which may be trapped about the prosthesis. In this respect it will be appreciated that, inasmuch as the interior of system 5 was purged with carbon dioxide prior to being filled with saline, any gas bubbles which might still remain in the interior of the system even after such shaking will be harmless carbon dioxide bubbles, rather than dangerous air bubbles. In a preferred embodiment, a manifold device integral to the system, or temporarily attached thereto, purges air from the system prior to cutting an incision. This manifold device has hoses connected to it from a suction source, a $CO_2$ source and a saline source. The manifold also has an "OFF" position. To purge the blood access system, the surgeon will first apply suction to the system to evacuate most of the air; then fill the system with $CO_2$ to displace any remaining oxygen; and finally fill the system with saline. Any remaining bubbles will mostly be harmless $CO_2$. Alternatively, this device could be a separate manifold tool used to purge any device that might inject air to the circulatory system and be inserted to the blood access system through one of the access seals 60.

A scalpel is then inserted into an instrument port on the system, and an incision is made through the left atrium wall from the inside of the system. This incision is made within the perimeter of the aforementioned running stitch so as to avoid cutting the suture.

Then base 15 of the system, which is flexible and stitched to the wall of the heart, is pulled apart so as to cause the incision to open wide. In this way, a 2 inch incision will yield an approximately 1 inch diameter hole through the wall of the left atrium. However, due to the column of fluid (i.e., saline) contained in system 5, as well as the presence of seals 60, effectively no bleeding will occur.

The prosthetic valve, which was previously placed within the interior of the system, may now be passed through the wall of the left atrium and into position within the heart. Instruments may then be safely and easily passed through the system so as to secure the prosthetic valve in position within the heart.

Once the prosthesis is secured in position within the heart, the instruments are removed from the system, and then the running stitch is pulled tight so as to close the incision in the wall of the left atrium.

Finally, the system is removed from the heart, e.g., by unstitching stitching cuff 50 from the wall of the heart, and then the incision is permanently closed with additional suture or staples while being held closed with the running stitch.

Figure 7:
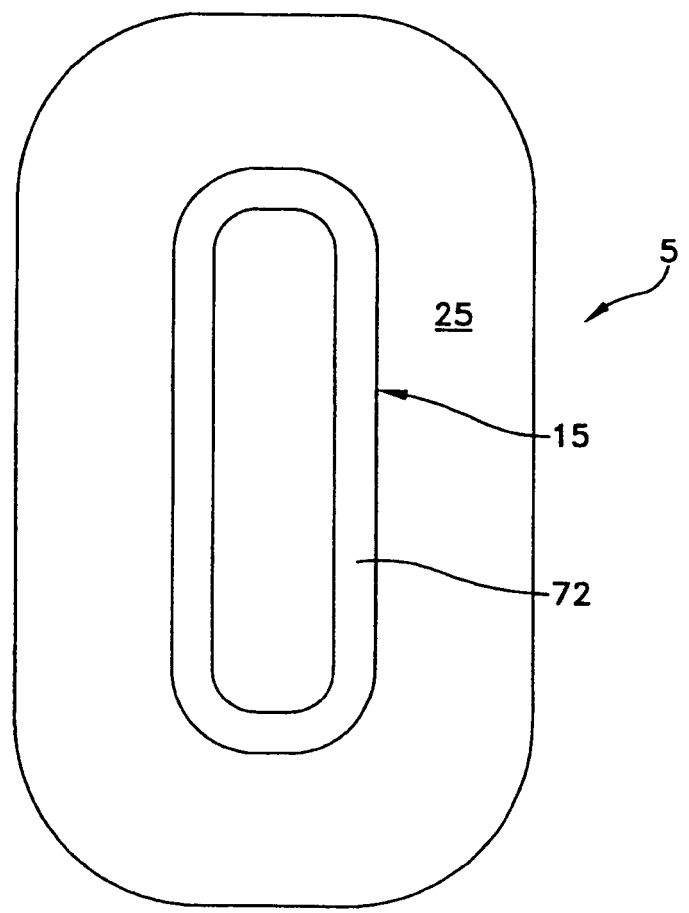
FIG. 7 is a bottom view of another alternative form of the invention.

Looking next at FIGS. 6 and 7, several alternative embodiments are illustrated for attaching system 5 to a cardiovascular structure.

More particularly, in FIG. 6 there is shown a releasable vacuum lock 65 which is adapted to securely attach system 5 to the wall of the heart with a fluidtight seal. Releasable vacuum lock 65 comprises a groove 70 formed in the floor 72 of base 15 and a vacuum fitting 75 communicating therewith, such that when base 15 is positioned against the outer wall of the heart, and a vacuum source is connected to vacuum fitting 75, system 5 may be releasably attached to the wall of the heart through suction.

In another alternative embodiment, and looking now at FIG. 7, the floor 72 of base 15 is adapted to be glued to the outside wall of the heart, whereby to secure the base of system 5 to the wall of the heart. At the conclusion of the cardiac procedure, in order to remove system 5 from the wall of the heart, the system's tapered wall 25 is cut away from base 15. Base 15 may then be left permanently attached to the outside wall of the heart. Any system remnant left attached to the outside of the heart at the conclusion of the procedure should be a soft, flexible material that will not constrain the contractibility of the heart during distole or systole. Additionally, any remnant left on the heart may be over-sewn so as to assure an air-tight seal.

Figure 8:
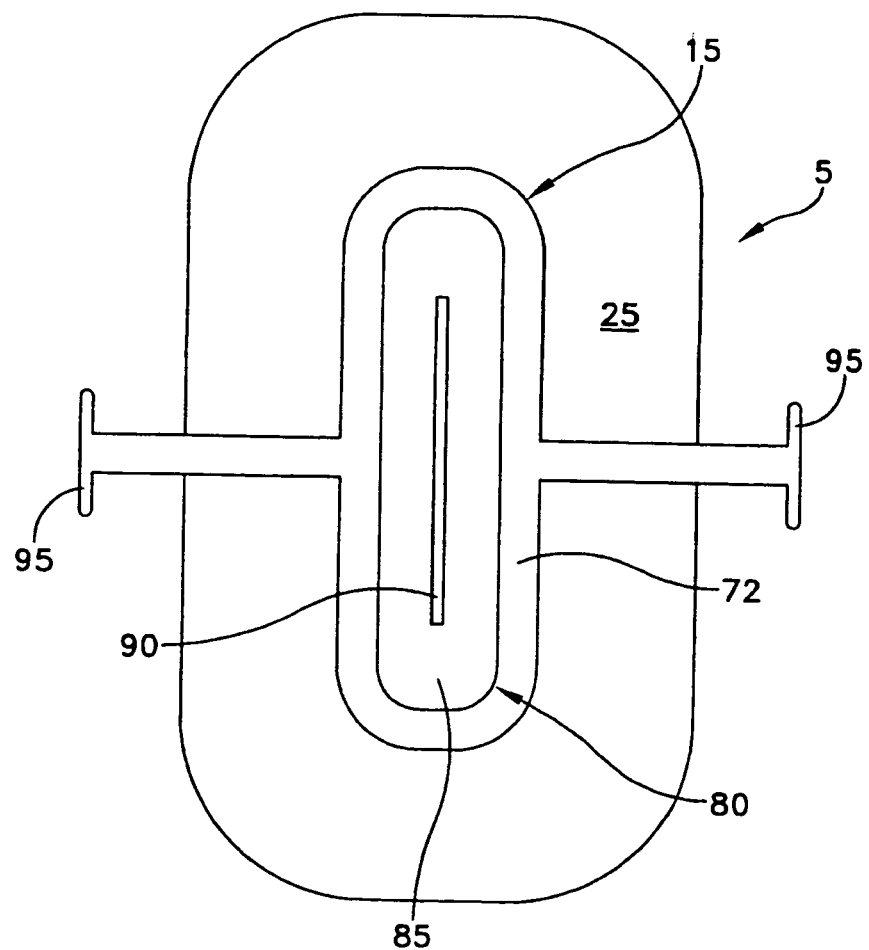
FIG. 8 is a bottom view of still another alternative form of the invention.

Looking next at FIG. 8, a blade guide 80 is provided at base 15 of system 5. Blade guide 80 is adapted to guide a cutting tool (not shown) during an incision through the wall of the heart. To this end, blade guide 80 includes a floor 85 which is resistant to penetration by a cutting blade. This floor 85 may or may not be formed integral with the floor 72 of base 15. Floor 85 includes an opening 90 therein. Opening 90 is initially in the form of a narrow slit so as to act as a guide for a cutting tool when that cutting tool is making an incision through the wall of the heart. This guide may relate to both the perimeter of the incision and the depth of the incision. Floor opening 90 is also adapted to allow larger objects, including prosthetic devices and surgical instruments, to pass through blade guide 80 and then through the wall of the heart. To this end, a pair of tabs 95 are provided for pulling the sides of base 15 outward, whereby to enlarge opening 90 and allow larger objects to pass by the blade guide. In this respect it will be appreciated that inasmuch as the system's base 15 is secured to the wall of the heart when tabs 95 are pulled apart, enlargement of opening 90 will be accompanied by enlargement of the incision as well.

Figure 9:
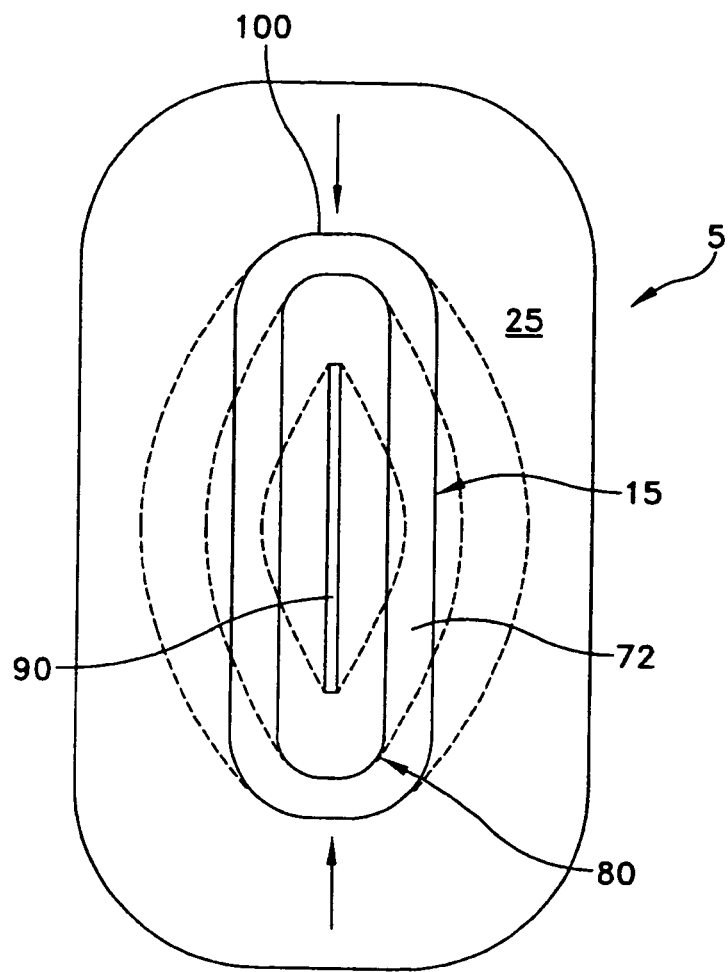
FIG. 9 is a bottom view of yet another alternative form of the invention.

Looking next at FIG. 9, in another alternative embodiment, system 5 has a narrow, flexible base 15 having opposing ends 100, 105 and containing blade guide 80. Base 15 is attached to the wall of the heart as described above using suture cuff 50, releasable vacuum lock 65, or glued floor 72 (this latter configuration is depicted in FIG. 9). An incision is made through blade guide 80 into the wall of the heart. Ends 100, 105 are then pushed toward one another so as to expand base 15 of system 5. Expansion of base 15, which is attached to the wall of the heart, increases the openings of both blade guide opening 90 and the incision. A prosthetic device and other objects may then be introduced through the increased opening in blade guide opening 90 and the increased opening of the incision. Blade guide opening 90 and the incision in the wall of the heart may thereafter be closed by simply relaxing the pressure on opening base ends 100, 105. In the preferred embodiment, instruments may be passed through, and manipulated in, the "closed" position of the incision.

Figure 10:
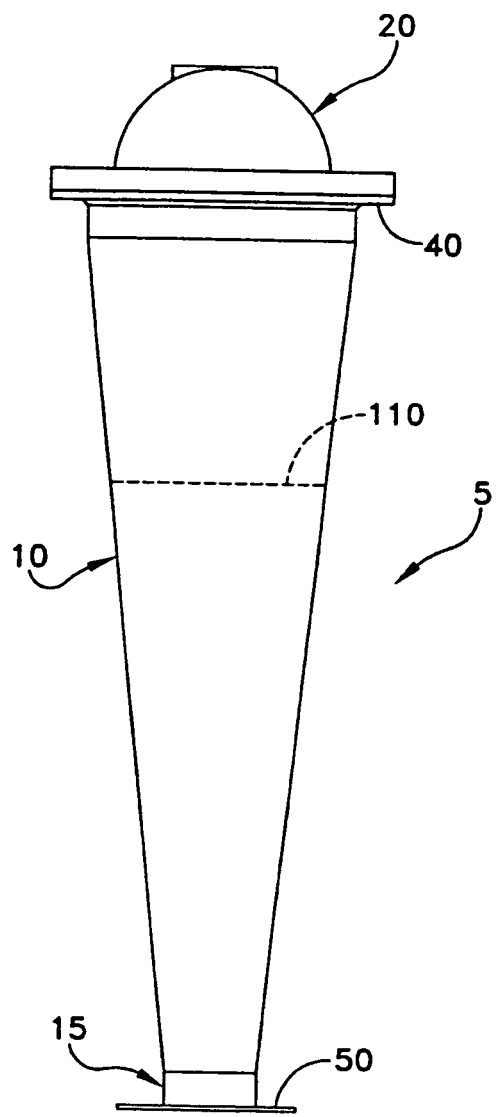
FIG. 10 is a side view of another alternative form of the invention.

In another preferred embodiment, and looking now at FIG. 10, blood lock 5 is provided with a relatively tall main body 10. System 5 is partially filled with fluid and the level 110 of fluid rises and falls with each beat of the heart. This configuration is possible due to the relatively low pressure, i.e., about 5-10 mm Hg, inside the atriums of the heart and the pulmonary veins. This configuration can be advantageous in that a reliable fluid lock is maintained even if cover 20 should be removed intermediate the procedure, e.g., to receive another prosthetic device and/or oversized instruments.

Figure 11:
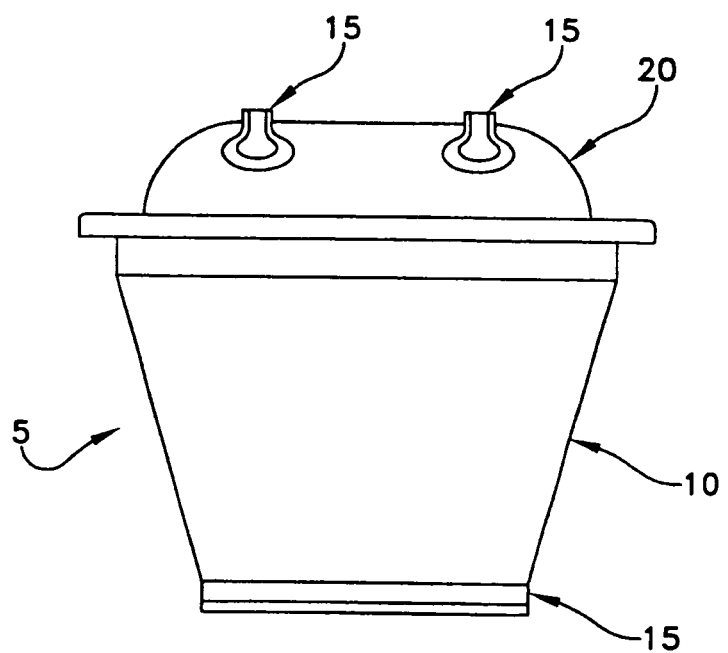
FIG. 11 is a front view of still another alternative form of the invention.

As noted above, blood lock 5 contains seals 60 for selectively closing off its instrument ports 55B and 55C. Examples of such seals are cruciform seals, conical seals and other simple seals. Seals 60 may also include more complex structures such as the articulating seals 115 shown in FIG. 11, whereby to allow greater manipulation of various instruments through the seals.

As also noted above, the incision in the wall of the heart is closed off at the conclusion of the intravascular procedure. In one preferred form of the invention, the running stitch of FIGS. 5A-5C is used. Several additional constructions are described below for closing off the incision in the heart wall.

Figure 12:
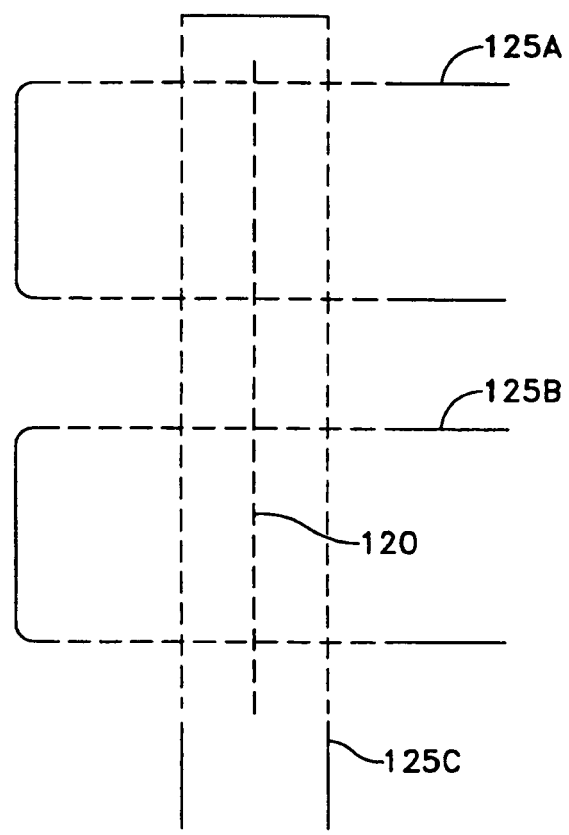
FIGS. 12 and 13 illustrate the formation and closure of alternative pursestring stitches which may be used in conjunction with the present invention.
Figure 13:
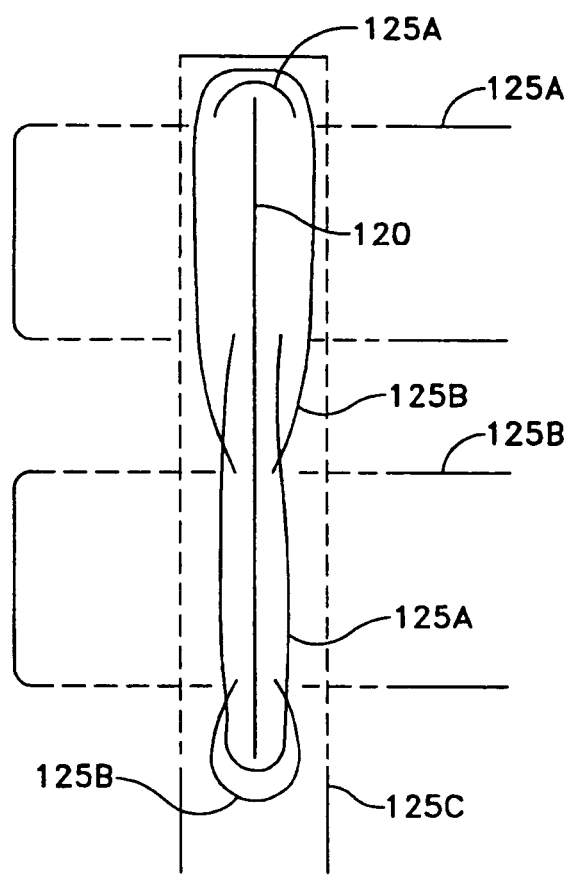

In one preferred construction, and looking now at FIGS. 12 and 13, the incision 120 is preliminarily closed after the intravascular procedure is completed using multiple pursestring stitches 125A, 125B and 125C. Pursestring stitches 125A, 125B and 125C are pre-positioned as shown in FIG. 12. Then the bodies of the pursestring stitches 125A and 125B are pulled so as to open a place for incision 120 (FIG. 13). After attachment of system 5 to the wall of the heart, incision 120 is made within the perimeter of the extended pursestring stitches 125A and 125B, and within the perimeter of pursestring stitch 125C. At the end of the procedure, each pair of pursestring ends are pulled so as to draw each pursestring stitch tight and thereby close incision 120 along its length without causing bunching in the wall of the heart. Then system 5 is removed as described above.

Figure 14:
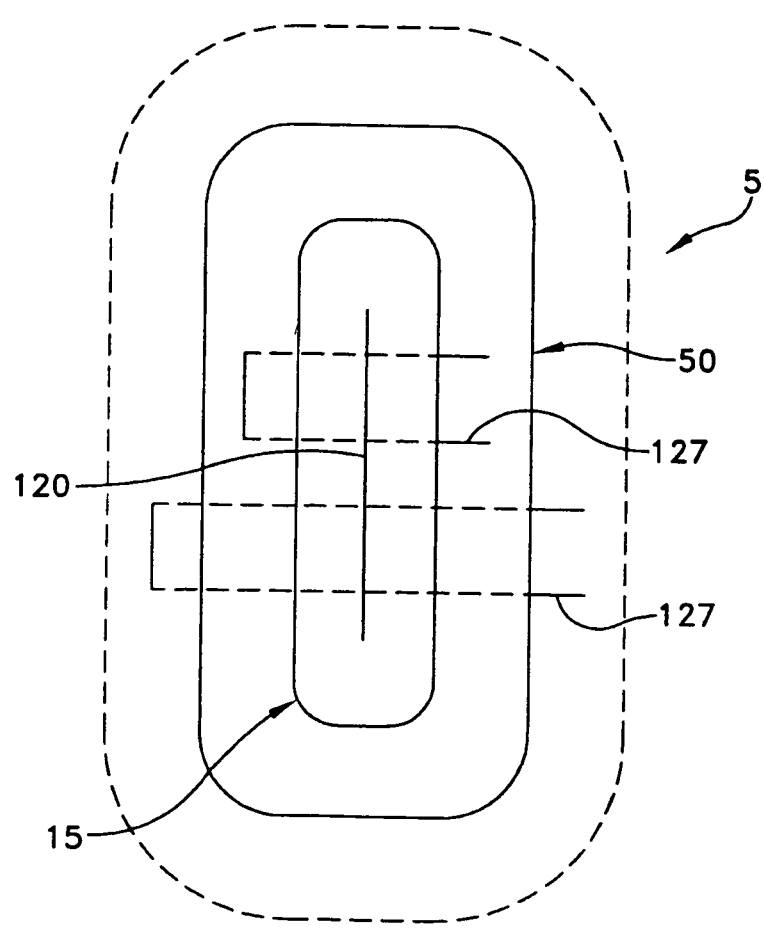
FIG. 14 is a schematic bottom view showing an alternative method for closing an incision at the conclusion of the procedure.

In another preferred embodiment, the incision is closed off by suturing prior to removal of system 5 from the wall of the heart, as illustrated in FIG. 14. In this case, instead of pre-positioning a closing suture, such as a running stitch, in the region where the system will be placed, system 5 is simply attached to the wall of the heart. At the conclusion of the intravascular procedure, incision 120 is sutured closed by simply placing sutures 127 through, or outside of, system 5. After incision 120 is sutured closed, all or part of system 5 is removed from the wall of the heart. Additional suturing to close incision 120 may also be preformed after the removal of system 5.

Figure 15:
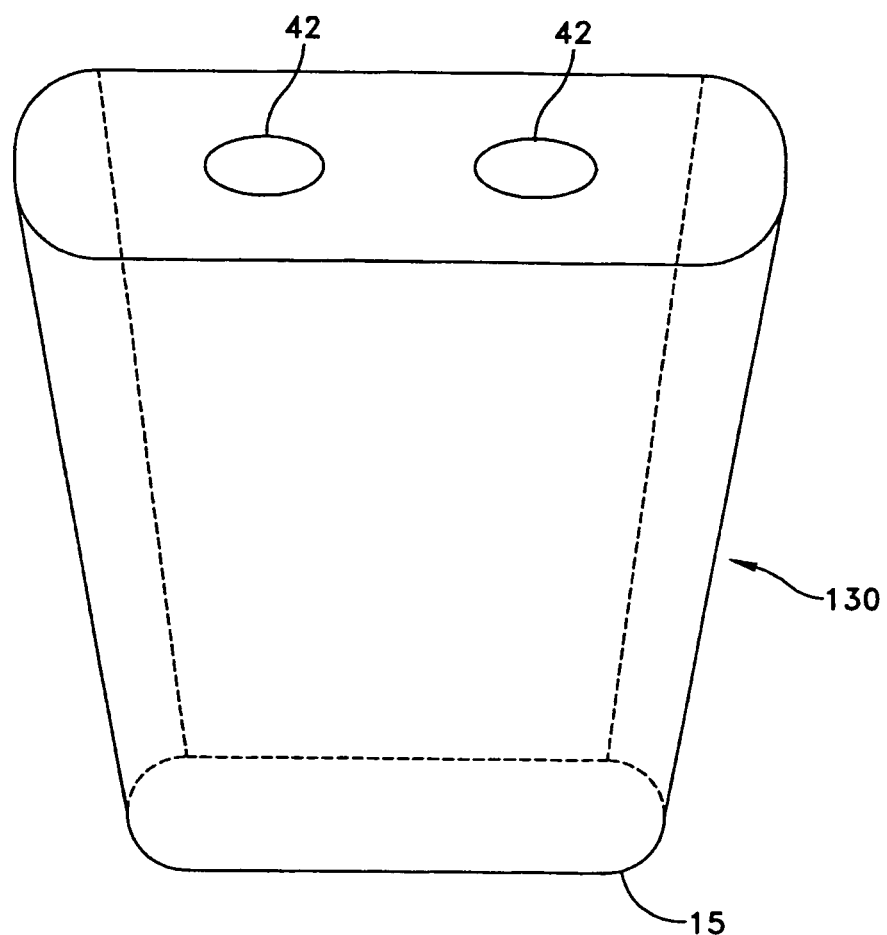
FIG. 15 is a schematic view of yet another form of the present invention.

In another preferred embodiment, cover 20 is formed integral with main body 10 so as to form a closed container 130, shown in FIG. 15. Base 15 is open so as to allow introduction of a prosthesis to the interior of the system prior to the attachment of the system to the wall of the heart. Closed container 130 includes one or more ports 40 to introduce instruments during the intravascular procedure. After attachment of base 15 to the wall of the heart, ports 40 are the only exposure to the outside environment. This configuration may provide a greater integrity of system 5 as cover 20 cannot be removed during the procedure, however, the prosthesis cannot be changed during the intravascular procedure due to the permanent closure of the top end of the system.

In addition to the foregoing, the container 130 shown in FIG. 15 can be formed with a closed bottom wall. In this configuration, the prosthesis is pre-loaded into container 130 at the time of manufacture; thereafter, during use, after the container 130 has been filled with saline, a sharp cutting instrument is introduced through a port 40 and used to simultaneously cut through the system's closed bottom wall and the wall of the heart. Furthermore, if desired, container 130 could be pre-filled with saline at the time of manufacture, and its closed bottom wall could be pre-coated with an adhesive at the time of manufacture, with the adhesive being covered by a peel-off tab until use.

Figure 16:
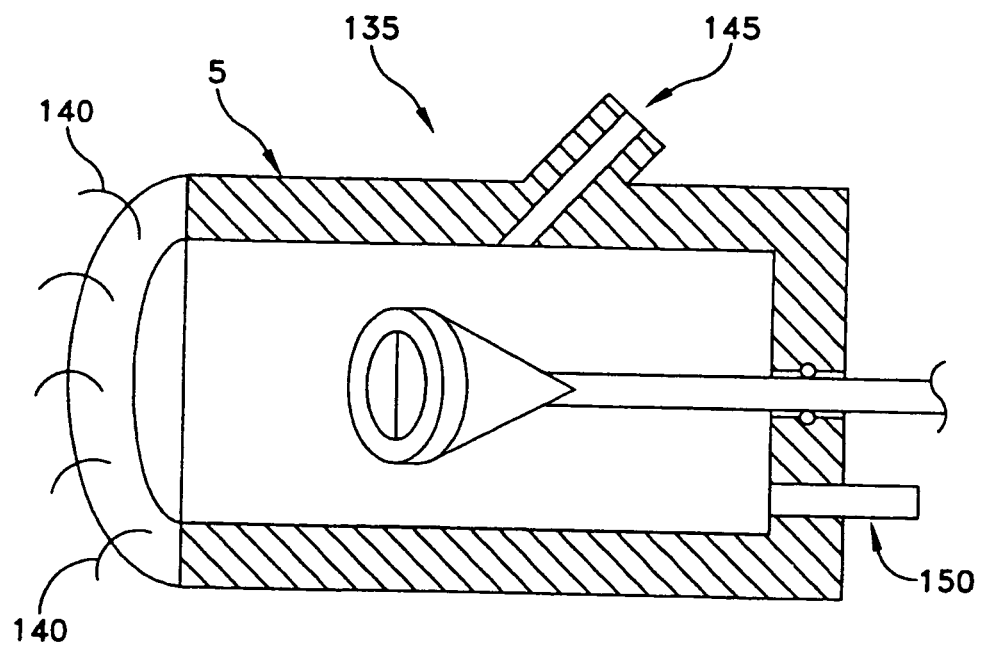
FIGS. 16-18 are views of still another form of the present invention.
Figures 17, 18:
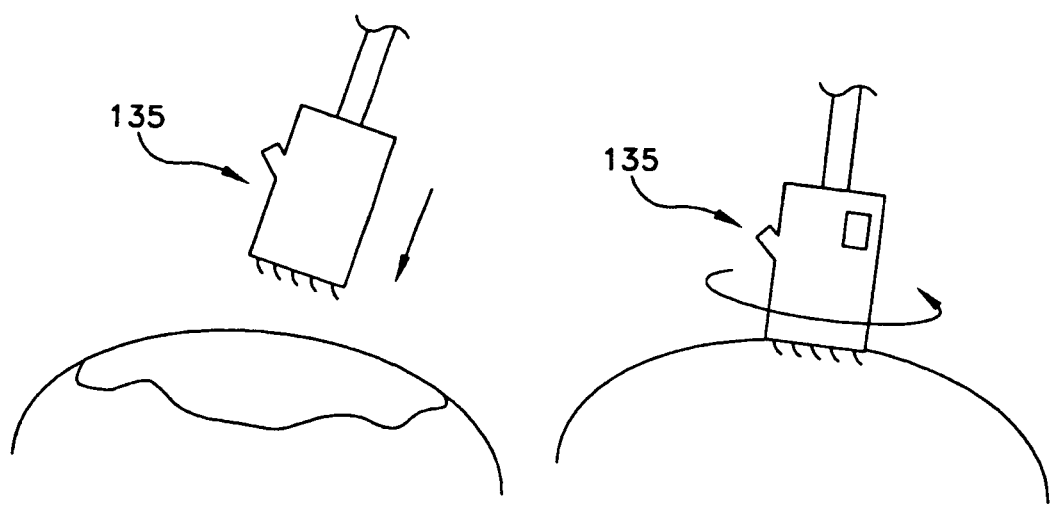

Now looking at FIGS. 16-18, the system 5 may also be formed as part of a tool 135. Tool 135 includes hooks 140 to secure tool 135 to the wall of the heart. An access port 145 is provided for insertion of a scalpel, and a port 150 is provided for connection to a purge line. Tool 135 is used by simultaneously plunging and turning hooks 140 into the wall of the heart so as to secure tool 135 to the heart (FIG. 18).

Figure 19:
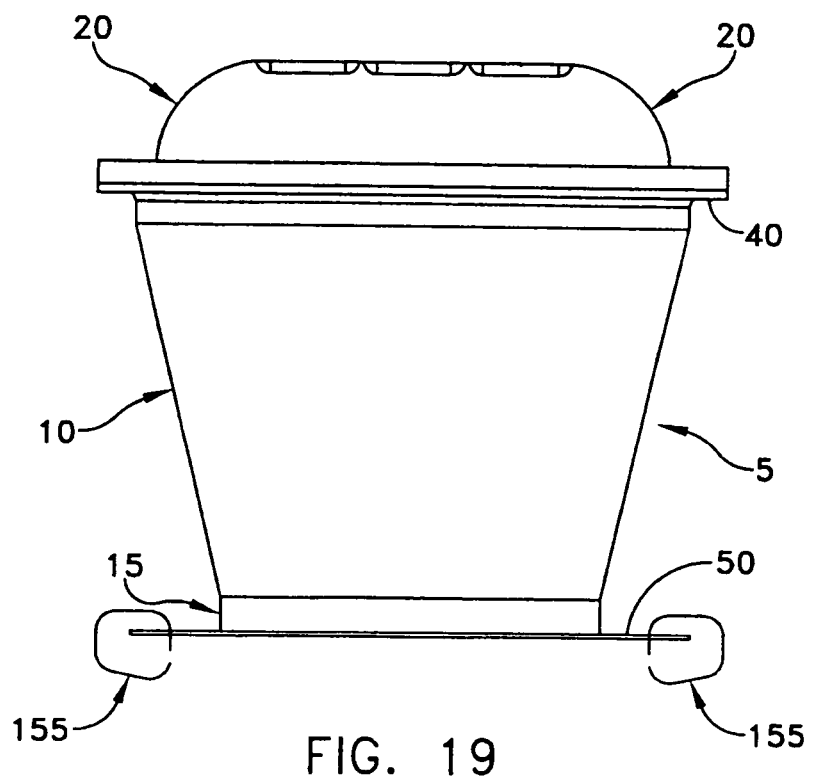
FIG. 19 is a front view of the present invention, showing staples attaching the system to tissue.

Now looking at FIG. 19, a system 5 is shown with staples 155 delivered to its stitching cuff 50 so as to secure the system to the wall of the heart. Staples 155 may be delivered by a complex stapling device.

Figure 20:
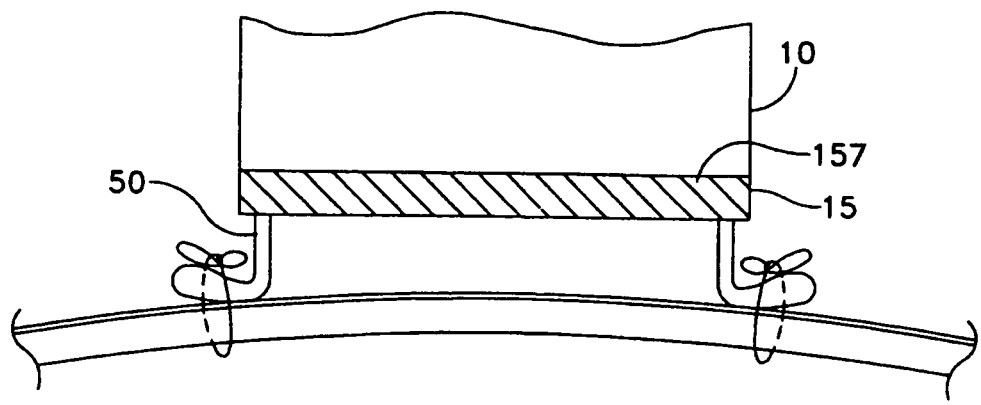
FIGS. 20 and 21 are views of an alternative device and method to close an incision at the conclusion of the procedure.
Figure 21:
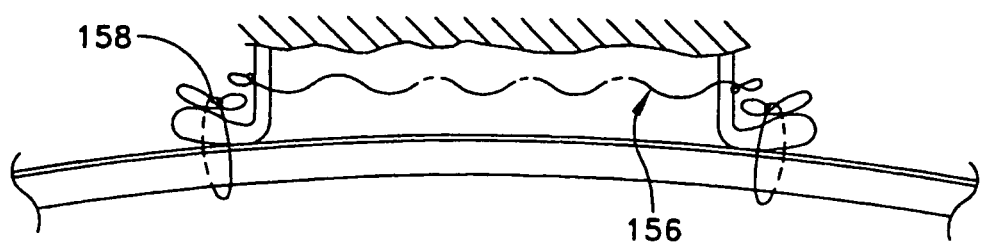

FIGS. 20 and 21 detail an alternative device and method to close the surgical incision 120. Without limiting the scope of this invention, the preferred embodiment of this device and method is to directly close stitching cuff 50 with suture 156, below the base 15 and as close to the surgical incision 120 as possible, which in turn holds incision 120 closed during the healing process. The closed stitching cuff 50 may then either be cut away or detached from the base 15 above cuff closing suture 156 but below the stitching cuff interface 157. This interface 157 is created during the manufacturing process and may be any one of a number of fixation methods such as sewing, stapling, insert molding or mechanical crimping. This interface may also be the position where the implanted stitching cuff 50 is removed from the base 15.

FIG. 21 shows the implanted stitching cuff 50, closed with closing suture 156. It is also envisioned that closing suture 156 may be one of many closing mechanisms such as wire, staples or adhesives. Additionally, in case of an emergency, the surgeon may quickly close the open incision 120 by placing a large hemostat across the stitching cuff along the same path of closing suture 156 as shown in FIG. 21. Additionally, as described earlier, suture cuff 50 may be attached to the surgical site via sutures 158 or hooks 140 or staples 155 or adhesive or other appropriate attaching means.

What is claimed is:

1. A method for providing access to a functioning vascular system of a patient, said method comprising:
    positioning an apparatus for providing access to a functioning vascular system of a patient at least partially against tissue of a functioning vascular system, said apparatus comprising:
        a main body having sidewalls defining an interior region and an exterior region, and a bottom end and a top end;
        a base being formed at said bottom end of said main body, securing means being configured on said base so as to allow attachment and formation of a seal between said base and the functioning vascular system of the patient, and said base being configurable to provide a passageway from said interior region of said main body to the functioning vascular system of the patient; and
        a removable cover provided at said top end of said main body, wherein said cover, when closed, provides a barrier between said interior region and said exterior region at said top end of said main body;
    attaching said securing means of said base to a selected portion of the functioning vascular system of the patient;
    forming an incision in said selected portion of the vascular system of the patient within an interior boundary of said base in attachment thereto;
    changing the configuration of said base so as to selectively change the incision to be more open as formed in said selected portion of the vascular system of the patient;
    passing an instrument through said incision as opened by configuring said base and as is formed in said selected portion of the vascular system of the patient;
    closing said incision in said selected portion of the vascular system of the patient within said interior boundary of said base in attachment thereto; and
    removing at least a portion of said apparatus from the functioning vascular system of a patient.

2. A method according to claim 1, wherein the step of changing the configuration of said base includes pulling said base apart.

3. A method according to claim 1 wherein the base is positioned entirely outside of the incision during the step of changing the configuration of the base.

4. A method according to claim 1 wherein the cover has a length and width both of which are greater, respectively, than a length and a width of the base.

5. A method according to claim 1 wherein the main body includes a mount to which the cover is secured and further wherein the base is oriented parallel to the mount.

* * * * *